United States Patent [19]
Jackson

[11] Patent No.: US 6,237,591 B1
[45] Date of Patent: May 29, 2001

(54) TURBINE DRY POWDER INHALER

(75) Inventor: Thomas R. Jackson, San Diego, CA (US)

(73) Assignee: Dura Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/184,821

(22) Filed: Nov. 2, 1998

(51) Int. Cl.[7] ............... A61M 15/00; A61M 16/00; B05D 7/14; B65D 83/06
(52) U.S. Cl. ............... 128/203.15; 128/203.12; 128/203.21
(58) Field of Search ............... 128/203.12, 203.15, 128/203.21; 604/58, 57

(56) References Cited

U.S. PATENT DOCUMENTS

| 16,066 | 11/1856 | Murphy . | |
|---|---|---|---|
| D. 384,283 | 9/1997 | Davies et al. . | |
| 2,147,435 | * 2/1939 | Gehrcke | 128/203.15 |
| 3,362,405 | * 1/1968 | Hazel | 128/203.15 |
| 3,507,277 | 4/1970 | Altounyan et al. . | |
| 3,518,992 | 7/1970 | Altounyan et al. . | |
| 3,669,113 | 6/1972 | Altounyan et al. . | |
| 3,807,400 | 4/1974 | Cocozza . | |
| 3,831,606 | 8/1974 | Damani . | |
| 3,837,341 | 9/1974 | Bell . | |
| 3,948,264 | * 4/1976 | Wilke et al. | 128/203.15 |
| 3,971,377 | * 7/1976 | Damani | 128/203.15 |
| 4,147,166 | * 4/1979 | Hansen | 128/203.15 |
| 4,452,239 | 6/1984 | Malen . | |
| 4,466,327 | 8/1984 | Hinton . | |
| 4,524,769 | * 6/1985 | Wetterlin | 128/203.15 |
| 4,739,754 | * 4/1988 | Shaner | 128/203.15 |
| 4,811,731 | 3/1989 | Newell et al. . | |
| 5,033,463 | 7/1991 | Cocozza . | |
| 5,207,217 | 5/1993 | Cocozza et al. . | |
| 5,327,883 | 7/1994 | Williams et al. . | |
| 5,372,128 | 12/1994 | Haber et al. . | |
| 5,492,112 | 2/1996 | Mecikalski et al. . | |
| 5,577,497 | 11/1996 | Mecikalski et al. . | |
| 5,921,237 | 7/1999 | Eisele et al. . | |
| 5,983,893 | * 11/1999 | Wetterlin | 128/203.15 |
| 6,006,747 | * 12/1999 | Eisele et al. | 128/203.15 |

FOREIGN PATENT DOCUMENTS

| 0 069 715 | 1/1983 | (EP) . | |
|---|---|---|---|
| 0 495 675 | 7/1992 | (EP) . | |
| 1295081 | 11/1972 | (GB) . | |
| 2 264 237 | 8/1993 | (GB) . | |
| 91/02558 | * 3/1991 | (WO) | 128/203.15 |

OTHER PUBLICATIONS

Spinhaler—Fisons, p. IV–2 (single page with diagram entitled "Spinhaler: Active transfer to airstream").

* cited by examiner

Primary Examiner—Glenn K. Dawson
Assistant Examiner—Joseph F. Weiss, Jr.
(74) Attorney, Agent, or Firm—Lyon & Lyon LLP

(57) ABSTRACT

A turbine powered inhaler has a propeller mounted on a turbine shaft within an aerosolizing chamber. An air pathway extends from an inlet, through the turbine to the aerosolizing chamber, and out through a mouth piece. Upon inhalation by a patient, air flowing through the air path rapidly spins up the turbine which directly drives the propeller within the aerosolizing chamber. Air and drug particles are mixed and de-agglomerated in the aerosolizing chamber via the spinning propeller, without the need for a motor and batteries.

22 Claims, 4 Drawing Sheets

TURBINE DRY POWDER INHALER

BACKGROUND OF THE INVENTION

Figure 1:
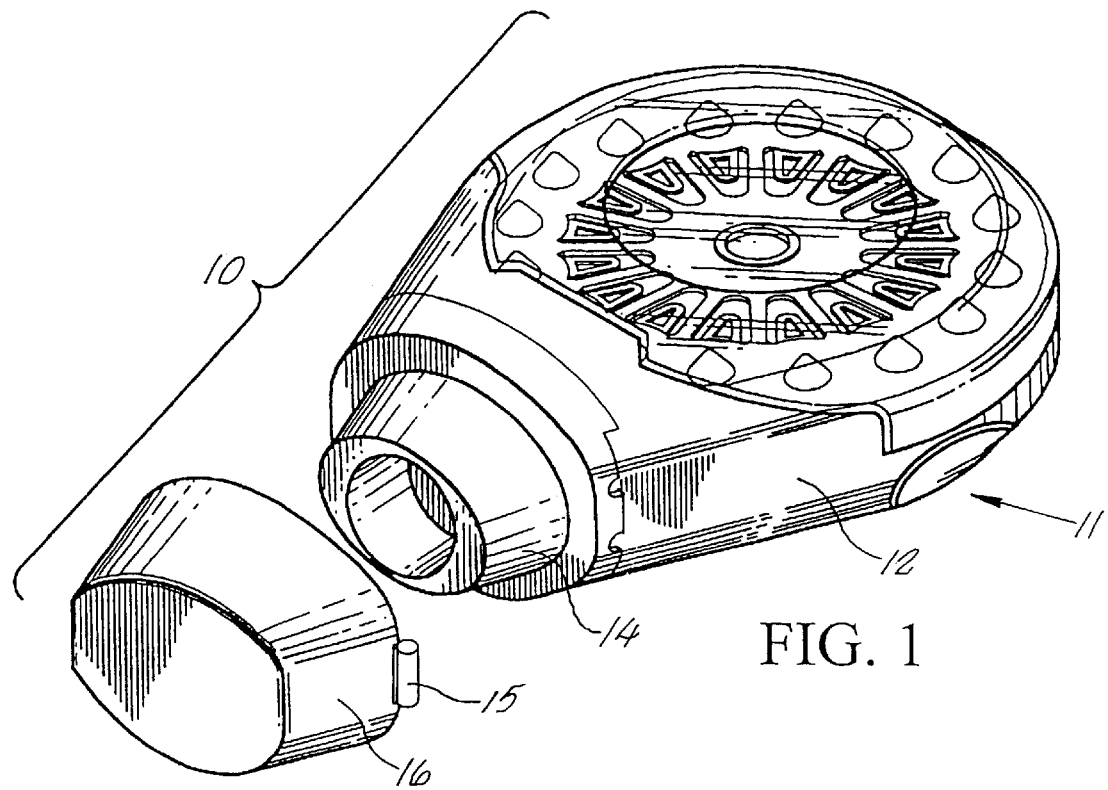
Figure 2:
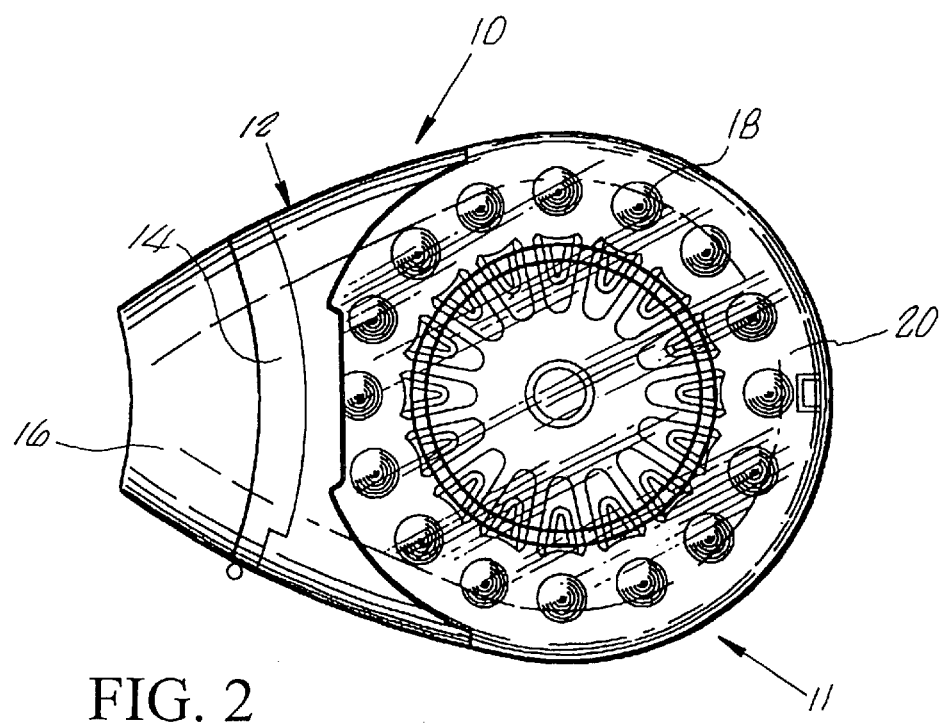
Figure 3:
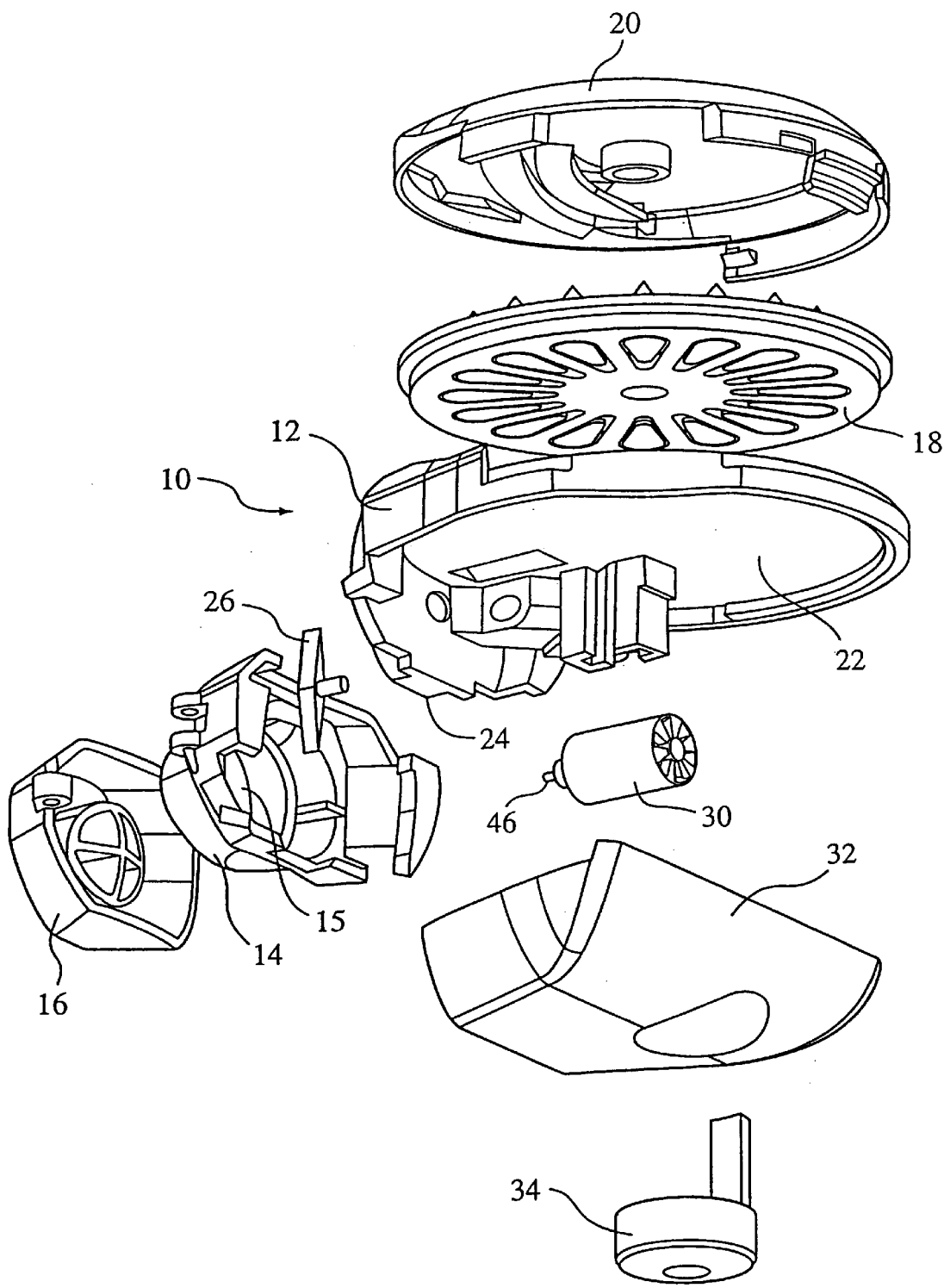
Figure 4:
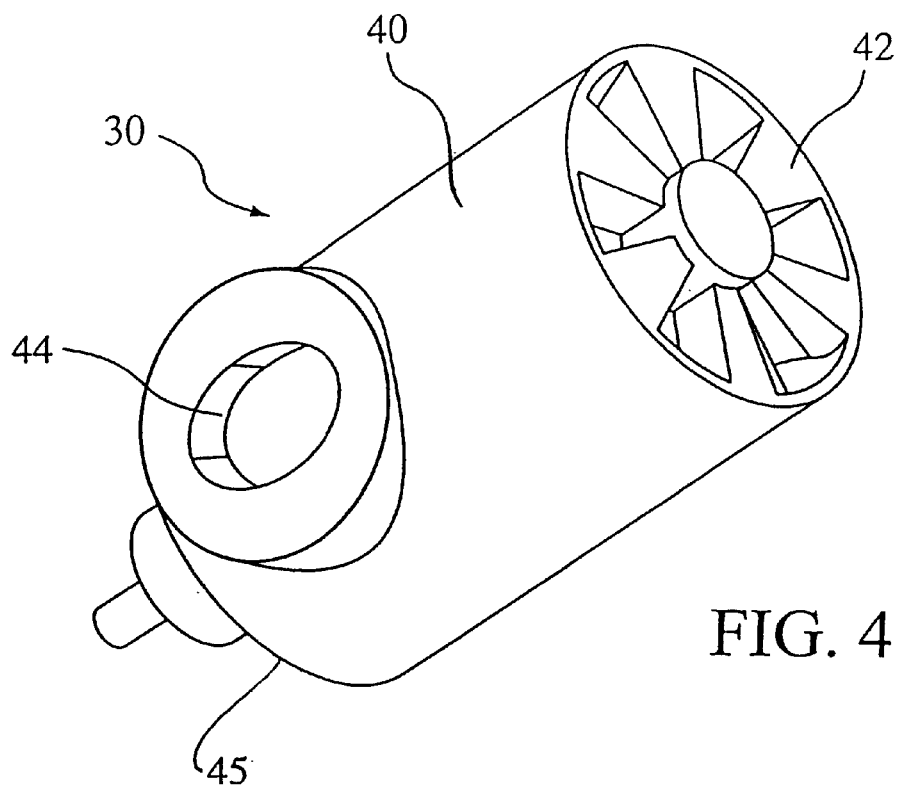
Figure 5:
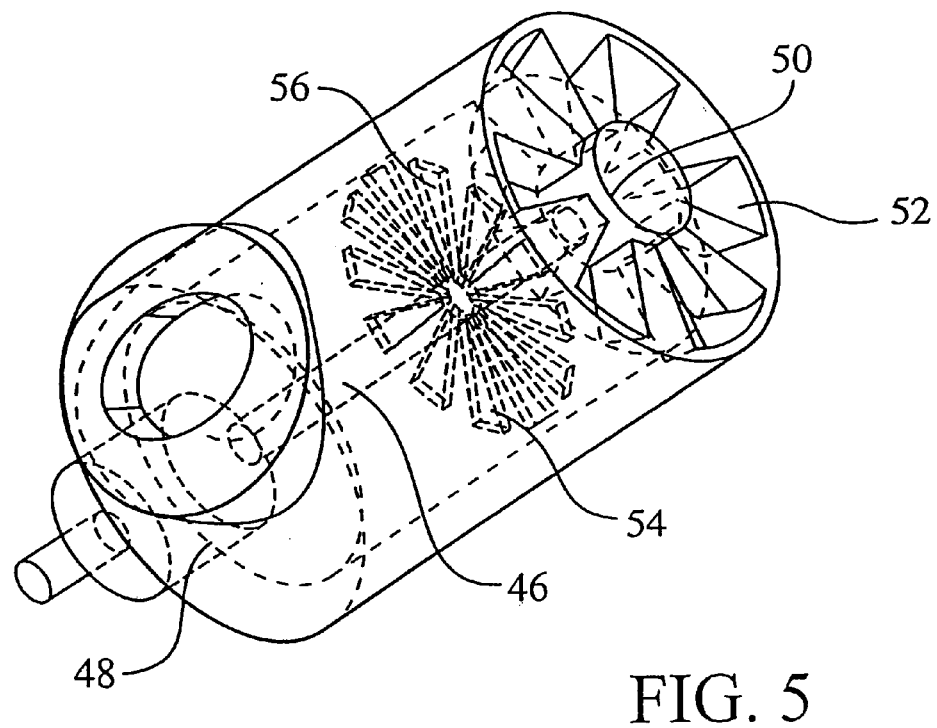

The field of the invention is inhalers for delivering dry powder pharmaceuticals to the lungs.

Inhalers have long been used to deliver pharmaceuticals into a patient's lungs. Dry powder inhalers provide a mixture of a dry powder pharmaceutical and air to the patient. The air/pharmaceutical powder mixture is delivered via the patient inhaling from a mouthpiece on the inhaler. The Spiros® inhaler, described in U.S. Pat. Nos. 5,327,883 and 5,577,497, and U.S. Pat. Nos. 5,921,237 and 6,116,238, all incorporated herein by reference, hold great potential for improved delivery of dry powder pharmaceuticals to the lungs. These inhalers use a small electric motor which spins a propeller within an aerosolizing chamber. The spinning propeller efficiently mixes the air and powder pharmaceutical in the aerosolizing chamber, and also helps to separate the active drug particles from inactive carrier particles, increasing the respirable fraction of the pharmaceutical composition. However, the motor, batteries, switch, indicator lights, and related circuitry in these inhalers increase their manufacturing cost and complexity. Consequently, although these types of inhalers are greatly improved over prior inhalers and have performed very well in clinical tests, there remains a need for a dry powder inhaler having good efficiency yet with a simpler and less costly design.

Accordingly, it is an objection of the invention to provide a dry powder inhaler having the advantages of a propeller spinning within an aerosolizing chamber but with a simpler and less costly configuration than known inhalers.

SUMMARY OF THE INVENTION

To these ends, a dry powder inhaler has a turbine adjacent to an aerosolizing chamber. A turbine shaft extends out of the turbine and into the aerosolizing chamber. A propeller is mounted on the turbine shaft in the aerosolizing chamber. When the patient inhales, the turbine rapidly accelerates to a high rotational speed, driving the propeller within the aerosolizing chamber. As a result, the advantages provided by the propeller spinning within the aerosolizing chamber are largely realized, without the need for a motor and batteries, or other power source. Manufacturing cost and complexity are reduced. As the propeller and turbine are powered by the patient's inhalation, battery life is no longer a factor in inhaler operation, and the turbine inhaler may be used indefinitely, within the mechanical wear limits of the components.

BRIEF DESCRIPTION OF THE DRAWINGS

Other objects features and advantages will become apparent to those skilled in the art from the following drawings and descriptions. The drawings, which show a single embodiment, are provided for purposes of illustration only, and are not intended as a limitation of the forms of the invention.

In the drawings, wherein the same reference number denotes the same element, throughout the several views:

FIG. 1 is a perspective view of the present inhaler;

FIG. 2 is a plan view thereof;

FIG. 3 is an exploded perspective view thereof;

FIG. 4 is a perspective view of the inhaler shown in FIG. 3;

FIG. 5 is a perspective view thereof, also showing internal turbine details;

FIG. 6 is a schematic view showing air flow through the inhaler; and

FIG. 7 is an enlarged view of details shown in FIG. 6.

DETAILED DESCRIPTION OF THE DRAWINGS

Turning now in detail to the drawings, as shown in FIG. 1, an inhaler 10 has a mouthpiece 14 attached to a body 12. A mouth piece cover 16 is attached to the mouth piece 14 via a hinge 15. The mouth piece cover 16 can be pivoted open or removed during inhalation, or for cleaning.

Referring now to FIGS. 2 and 3, a blister disk 18 having a transparent cover 20 is mounted over a disk plate 22 attached to the body 12. An aerosolizing chamber 24 is formed in the front wall of the body 12.

A turbine 30 supported on the underside of the disk plate 22 has a turbine shaft 46 extending forwardly into the aerosolizing chamber 24. A propeller 26 is mounted on the forward end of the turbine shaft 46 in the aerosolizing chamber 24. A lower housing 32 encloses the bottom section of the disk plate 22. A plunger 34 extends through the lower housing 32, for opening blisters on the blister disk 18. The body 12 and lower housing 32 form an inhaler housing 11.

The design details and operation of the inhaler 10 are similar to the inhalers described in U.S. Pat. Nos. 5,622,166, and U.S. Pat. Nos. 5,921,237 and 6,116,238, incorporated herein by reference. However, the inhaler 10 has no motor, batteries, switch or circuitry. Rather, the spinning propeller 26 is powered purely by the turbine 30.

Referring to FIGS. 4–7, the turbine 30 has a cylindrical turbine housing 40. A stator 52 joined to the turbine housing 40 near the turbine inlet 42. A turbine outlet 44 is preferably positioned on one side of the cylindrical turbine housing 40, at the outlet end 45 of the turbine 30. The turbine shaft 46 is rotatably supported within the turbine housing 40 via a bushing 48 near the outlet end 45, and via a needle bearing 50 near the inlet end 42. A rotor 54 having pitched turbine blades 56 is attached and centered on the turbine shaft 46 adjacent to the stator 52.

Turning to FIGS. 6 and 7, and air inlet path 36 extends from the outside environment into the inhaler 10, and to the inlet end 44 of the turbine 30. A turbine outlet duct or path 60 runs from the turbine outlet 44 to a staging chamber 62 in the body 12 of the inhaler 10. An aerosolizing chamber duct 64 extends from the staging chamber 62 to the aerosolizing chamber 24. A chamber wall 15 in the mouth piece 14, as shown in FIG. 3 forms the front wall of the aerosolizing chamber 24, when the mouth piece 14 is attached on to the body 12. Openings in the chamber wall 15 allow the drug/air mixture to flow from the aerosolizing chamber 24 through the mouth piece 14 to the patient.

In use, a dose of dry powered drug is delivered into the staging chamber 62 from the blister disk 18, as described in U.S. Pat. Nos. 5,622,166 and U.S. Pat. Nos. 5,921,237, and 6,116,238. The patient places the lips over the mouth piece 14 and inhales. Upon inhalation, ambient air flows through the inlet air path 36 to the inlet end 42 of the turbine 30. The air flowing at right angles to the plane of the rotor 54 rapidly spins up the rotor and turbine shaft 46, simultaneously rapidly spinning up the propeller 26 which is directly mounted on to the front end of the turbine shaft 46. The rotor blades are pitched so that the air flow through the turbine, parallel to the axis of the turbine shaft, exerts torque, causing the rotor to spin. Air flows out of the turbine outlet 44 to the staging chamber 42. Dry powder pharmaceutical particles are entrained in the air flow and carried through the aerosolizing chamber duct 64 into the aerosolizing chamber 24.

The particles are de-agglomerated and mixed with air in the aerosolizing chamber 24. The air and particles pass out of the aerosolizing chamber 24 through openings in the chamber walls 15 and into the patient's mouth, throat, and lungs.

Preferably, the turbine is designed to that the turbine shaft will spin at from 5,000–15,000 rpm with an inspiration flow rate of 20–40 liters per minute. Most preferably, the turbine 30 is designed so that it spins up to 10,000 rpm or greater, within 100 milliseconds, with an inspiration flow rate of about 30 liters per minute. The stator 52 may have fixed vanes to better direct air flow to the rotor 54. Additional rotors 54 may optionally be added to the shaft 46.

The air flow through the inhaler 10 is substantially sealed, so that all air inhaled by the patient passes through the inlet air path 36, the turbine 30, the turbine outlet duct 60, the aerosolizing chamber duct 64, the aerosolizing chamber 24, and out through the mouth piece 14. For embodiments not having a separate dump chamber, air flowing out of the turbine may go directly into the aerosolizing chamber. Alternatively, a fraction of the total airflow into the patients lungs may be either inletted or channeled through ducts in the mouthpiece or inhaler to help beneficially entrain, mix, or guide the particle laden air mixture.

The turbine 30 may advantageously be provided as a separate subassembly installed into the inhaler 10 during manufacture. As a result, various other components of the inhaler, not requiring the precision tolerances necessary in the turbine, can be manufactured and assembled separately. The turbine is compact, preferably having a housing diameter of 1–2 centimeters.

Figure 6:
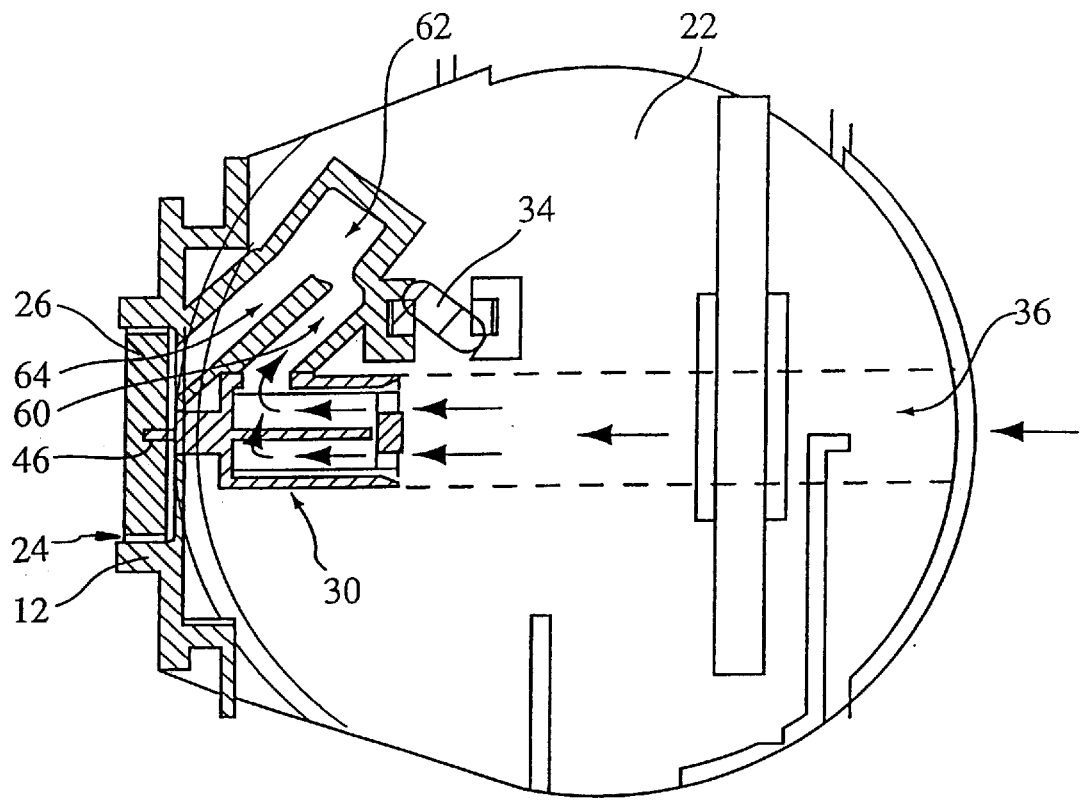
Figure 7:
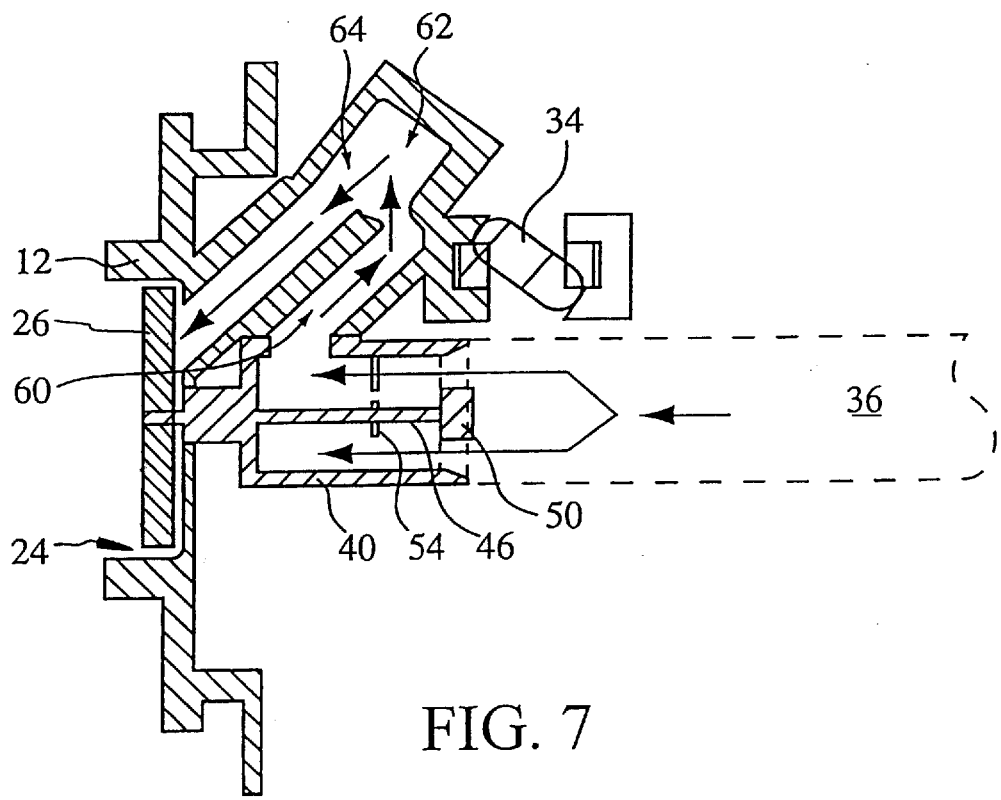

As shown in FIGS. 6 and 7, the dry powder does not flow through the turbine 30. Rather, the turbine 30 is upstream from the powder. The turbine therefore avoids clogging, friction, or bearing failure from powder particles, as the turbine is upstream of the powder. Although the turbine 30 uses the same air flow which entrains the powder, no balancing of air flow paths is required, and no coordination or timing of the spin-up of the turbine is needed, as the turbine automatically spins up upon inhalation.

The inhaler 10 consequently provides advantages of a motorized inhaler, without the need for a motor or batteries. If electronics are desired to provide an interface with the patient (for example, for dose counting, etc.) then very small batteries may be included to provide the typical low power requirements for such circuitry.

It may be desirable to allow the turbine enough time to reach a minimum acceptable rotary speed to de-agglomerate the drug, before the drug has passed through and out of the aerosolization chamber. One technique for this is to delay the introduction of the pharmaceutical mixture into the aerosolization chamber by sizing the length and diameter of the air path leading to the staging chamber. This allows the turbine time to reach the desired minimum rotational speed. As one example, if the outlet duct 60 is 1 cm diameter and 2.5 cm long, during the initial period of inhalation, at a flow rate of 5 liters per minute, the air takes 24 ms to reach the aerosolizing chamber. During that interval the turbine has accelerated up to a sufficient minimum speed.

Alternatively the inhaler may be inverted so that the air flowing through the turbine and hence 'over' the open well containing the blister has to reach a high enough velocity (i.e., 23 liters per minute, depending on how the local geometry is configured) to 'lift' the particles out of the blister well due to Bernoull's principal, rather than the particles just falling out of the well due to gravity even before the inhalation has begun. This could act as a passive method for regulating when the drug is introduced to the system based on the airflow rate.

In another embodiment intended to have the drug particles exposed to the spinning propeller in the aerosolization chamber is to place the restrictor holes, or outlet holes, near the center of the chamber rather than at the periphery. This would act like a centrifugal size filter, i.e. the larger particles would be forced to the periphery where the most aggressive de-agglomeration takes place until they are small enough to reach the more centralized outlet holes.

Thus, a novel inhaler has been shown and described. Various changes and modifications may, of course, be made, without departing from the spirit and scope of the invention. The invention, therefore, should not be restricted, except by the following claims, and their equivalents.

What is claimed is:

1. An inhaler comprising:
   a housing;
   an aerosolizing chamber within the housing;
   a propeller within the aerosolizing chamber;
   a turbine adjacent to the aerosolizing chamber, the turbine having an inlet side and an outlet side;
   a turbine shaft extending out of the turbine and into the aerosolizing chamber, with the propeller linked to the turbine shaft;
   a first air pathway extending from an air inlet in the housing to an inlet side of the turbine; and
   a second air pathway extending from the outlet side of the turbine to the aerosolizing chamber.

2. The inhaler of claim 1 further comprising a stator on the turbine and a rotor on the turbine shaft.

3. The inhaler of claim 1 wherein the turbine outlet is oriented at an angle to the turbine inlet.

4. The inhaler of claim 1 wherein the turbine is configured to spin the turbine shaft at from 5000 to 15000 rpm with a flow rate of 20–40 liters/minute of air flowing through the turbine.

5. The inhaler of claim 1 further comprising a staging chamber in the second air pathway, between the turbine outlet and the aerosolizing chamber.

6. The inhaler of claim 1 further comprising a rotor attached to the turbine shaft, with the turbine shaft and rotor having an axis of rotation parallel to the direction of air flow through the turbine.

7. The inhaler of claim 6 where the second air pathway is configured so that air flowing through it lifts drug particles out of the staging chamber, and entrains the particles in the flowing air.

8. The inhaler of claim 1 with the aerosolizing chamber having outlet holes near the center of the chamber, for filtering particles by size.

9. The inhaler of claim 1 further comprising a mouthpiece on the inhaler connected to the aerosolizing chamber, and with the first and second air pathways, the aerosolizing chamber, and the mouthpiece forming a substantially sealed air flow path through the inhaler.

10. The inhaler of claim 1 where the second air pathways are configured to delay introduction of a dry powder into the aerosolizing chamber until after the propeller is spun up to a minimum speed.

11. The inhaler of claim 1 where the propeller has two blades.

12. The inhaler of claim 1 where the propeller is mounted on the turbine shaft.

13. The inhaler of claim 1 where the turbine shaft extends substantially from the turbine inlet to the turbine outlet.

14. The inhaler of claim 1 with the turbine having rotor blades oriented so that air flow from the turbine inlet exerts torque on the turbine shaft.

15. An inhaler comprising:

a housing;

an inlet in the housing;

an aerosolizing chamber within the housing;

a mouthpiece on the housing connecting with the aerosolizing chamber;

a propeller in the aerosolizing chamber;

a turbine within the housing and outside of the aerosolizing flow and coupled to the propeller; and an air path extending from the inlet, through the turbine, into the aerosolizing chamber, and out to the mouthpiece.

16. A method of providing a dose of an inhaled pharmaceutical to a patient, comprising the steps of:

providing a pharmaceutical powder into an aerosolizing chamber in an inhaler;

drawing air through a turbine as the patient inhales, thereby spinning a propeller, attached to the turbine, in the aerosolizing chamber;

mixing air and the pharmaceutical powder in the aerosolizing chamber via the spinning propeller.

17. The method of claim 16 wherein the air is drawn through the turbine in a direction perpendicular to the plane of a rotor in the turbine, passes through the aerosolizing chamber, and is then inhaled by the patient.

18. The method of claim 16 wherein the pharmaceutical powder is mixed with air flowing out of the turbine, to avoid having the powder contact the turbine.

19. The method of claim 16 where the turbine spins up to at least 10,000 rpm within a 100 millisecond interval.

20. The method of claim 16 where the turbine spins at from 5,000–15,000 rpm with the patient inhaling at 20–40 liters per minute.

21. The method of claim 16 further including the step of conducting all of the air drawn through the turbine into the aerosolizing chamber.

22. The method of claim 16 further comprising the step of delaying the providing of the pharmaceutical powder into the aerosolizing chamber by a delay interval, to allow the propeller to spin up to a minimum acceptable speed, before the powder is provided into the aerosolizing chamber.

* * * * *